United States Patent

Hamprecht et al.

Patent Number: 5,488,029
Date of Patent: Jan. 30, 1996

[54] HERBICIDAL N-[1,3,5-RIAZIN-2-YL)-AMINOCARBONYL]-BENZENESULFONAMIDES

[75] Inventors: Gerhard Hamprecht, Weinheim; Horst Mayer, Ludwigshafen; Karl-Otto Westphalen, Speyer; Matthias Gerber, Limburgerhof; Uwe Kardorff, Mannheim; Helmut Walter, Obrigheim, all of Germany

[73] Assignee: BASF Aktiengesellschaft, Ludwigshafen, Germany

[21] Appl. No.: 244,945

[22] PCT Filed: Feb. 16, 1993

[86] PCT No.: PCT/EP93/00364

§ 371 Date: Jun. 17, 1994

§ 102(e) Date: Jun. 17, 1994

[87] PCT Pub. No.: WO93/17001

PCT Pub. Date: Sep. 2, 1993

[30] Foreign Application Priority Data

Feb. 28, 1992 [DE] Germany .......... 42 06 146.6

[51] Int. Cl.⁶ .......... C07D 251/42; A01N 43/66
[52] U.S. Cl. .......... 504/212; 544/211
[58] Field of Search .......... 544/211; 504/212

[56] References Cited

U.S. PATENT DOCUMENTS

| | | | |
|---|---|---|---|
| 4,120,691 | 10/1978 | Levitt | 544/182 |
| 4,127,405 | 11/1978 | Levitt | 544/211 |
| 4,371,391 | 2/1983 | Levitt | 544/211 |
| 4,397,679 | 8/1983 | Sauers | 544/194 |
| 4,425,153 | 1/1984 | Adams, Jr. | 544/211 |
| 4,510,325 | 4/1985 | Meyer et al. | 544/211 |
| 4,515,624 | 5/1985 | Reap | 544/211 |
| 5,071,470 | 12/1991 | Mayer et al. | 544/211 |

FOREIGN PATENT DOCUMENTS

| | | |
|---|---|---|
| 0044209 | 1/1982 | European Pat. Off. |
| 044807 | 1/1982 | European Pat. Off. |
| 173312 | 3/1986 | European Pat. Off. |
| 4038430 | 6/1992 | Germany |
| 4105418 | 8/1992 | Germany |
| WO92/09608 | 6/1992 | WIPO |

Primary Examiner—John M. Ford
Attorney, Agent, or Firm—Keil & Weinkauf

[57] ABSTRACT

N-[(1,3,5-traizin-2-yl)-aminocarbonyl]-benzenesulfonamides of the general formula I

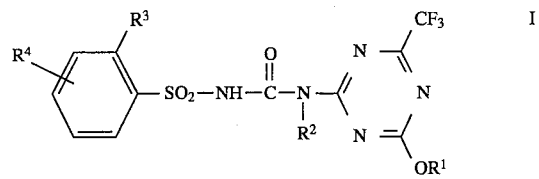

where $R^1$ is methyl or ethyl;

$R^2$ is hydrogen or methyl;

$R^3$ is substituted or unsubstituted alkyl;

a group $OR^5$ or $SR^5$ where $R^5$ is unsubstituted or fluorine-substituted alkyl, with the exception of difluoromethoxy; nitro or hydroxyl; and $R^4$ is hydrogen, methyl, ethyl, methoxy, ethoxy, methylthio, ethylthio, $C_1$- or $C_2$-haloalkoxy, fluorine or chlorine, with the exception of 6-chloro and 6-fluoro when $R^3$ is alkyl or $C_1$- or $C_2$-alkoxy;

and agriculturally useful salts thereof, processes for their preparation and the use thereof.

4 Claims, No Drawings

HERBICIDAL N-[1,3,5-RIAZIN-2-YL)-AMINOCARBONYL]-BENZENESULFONAMIDES

The present invention relates to N-[(1,3,5-traizin-2-yl)-aminocarbonyl]-benzenesulfonamides of the general formula I

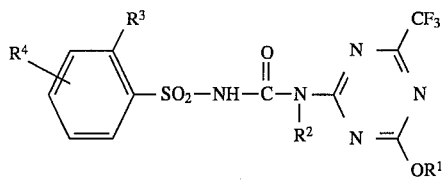

where $R^1$ is methyl or ethyl;

$R^2$ is hydrogen or methyl;

$R^3$ is $C_1$–$C_4$-alkyl which may carry from one to three methoxy groups;

$C_2$–$C_4$-haloalkyl;

a group $ER^5$ in which E is O or S and $R^5$ is $C_1$- or $C_2$-alkyl, $C_2$–$C_4$-alkenyl, $C_3$- or $C_4$-alkynyl or $C_3$–$C_6$-cycloalkyl which may carry from 1 to 3 or from 1 to 5 halogen atoms, with the exception of difluoromethoxy;

$NO_2$ or OH; and $R^4$ is hydrogen, methyl, ethyl, methoxy, ethoxy, methylthio, ethylthio, $C_1$- or $C_2$-haloalkoxy, fluorine or chlorine, with the exception of 6-chloro and 6-fluoro when $R^3$ is alkyl or $C_1$- or $C_2$-alkoxy;

and agriculturally useful salts thereof.

The present invention furthermore relates to a process for the preparation of the compounds I and to their use as herbicides.

The prior art includes a number of patents which relate to sulfonylureas having a herbicidal action.

U.S. Pat. No. 4,127,405 describes a triazine compound A and U.S. Pat. No. 4,169,719 the pyrimidine derivative B, which have the most similar structures.

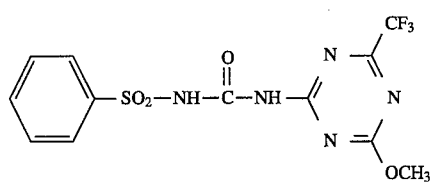

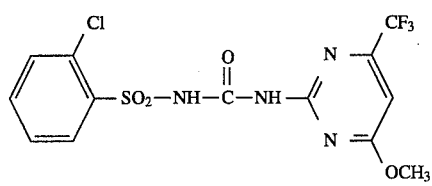

EP-A 44 807 describes two sulfonylureas C having an ortho allyloxy group.

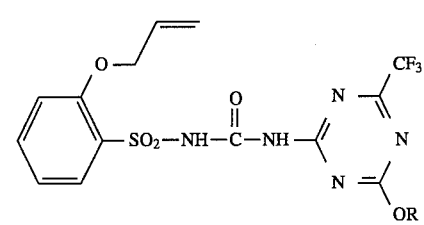

R=$CH_3$ or $C_2H_5$

EP-A 44 808 describes sulfonylureas D which are substituted by 2-chloroethoxy or difluoromethoxy in the phenyl moiety.

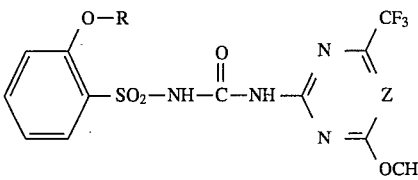

$D_1$:
Z=CH or N
R=$CH_2CH_2Cl$ $D_2$:
Z=N
R=$CHF_2$

EP-A 48 143 describes two N-methylated sulfonyl-ureas E, which are not further characterized.

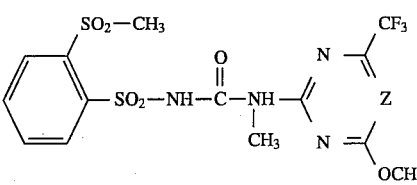

Z=CH or N

EP-A 388 873 relates to benzoates having the structure F.

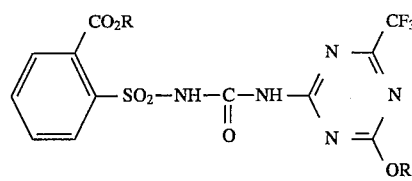

R=$CH_3$ or $C_2H_5$

U.S. Pat. No. 4,127,405 discloses sulfonylureas derivatives which are substituted by chlorine or trifluoromethyl in the ortho position of the phenyl ring and by $CH_3$/$OCH_3$ in the triazine ring

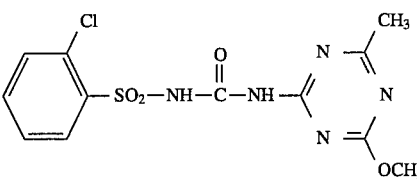

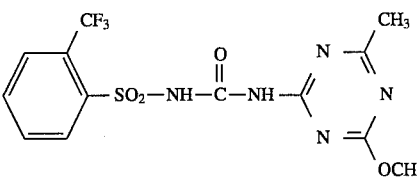

The compound G is known under the name chlorsulfuron (Glean®).

Sulfonylurea derivatives substituted by fluoroalkoxy, sulfamoyl, acyl or alkyl in the ortho position of the phenyl radical are represented by general formulae in EP-A 173 212, U.S. Pat. No. 4,515,624, U.S. Pat. No. 4 425 153 and EP-A 44 209, without more detailed information on specific structures being given.

The earlier German Applications WO 92/09608 of Dec. 1, 1990 and Wo 92/14715 of Feb. 22, 1991 describe herbicidal sulfonamides which, compared with the novel compounds, have different substituents in the ortho position of the phenyl radical and/or in the 3/5 positions of the triazine radical.

It is an object of the present invention to synthesize sulfonylureas which have improved properties compared with the known members of this herbicidal class and in particular exhibit high selectivity in sensitive crops, such as rice or corn.

We have found that this object is achieved by the N-[(1,3,5-traizin-2-yl)aminocarbonyl]-benzenesulfonamides of the formula I which are defined at the outset.

In view of their intended use, suitable substituents are, for example, the following:

$R^1$ is methyl or ethyl;

$R^2$ is hydrogen or methyl;

$R^3$ is $C_1$–$C_4$-alkyl, such as methyl, ethyl, n-propyl, isopropyl, n-butyl, isobutyl, sec-butyl or tert-butyl, which may carry from one to three methoxy groups, such as methoxymethyl or 2-methoxyethyl;

$C_2$–$C_4$-haloalkyl, such as 1-chloroethyl, 2-chloroethyl, 2-chloropropyl, 3-chloropropyl, 4-chlorobutyl, 1,1,2,2,2-pentafluoroethyl, 2,2,2-trifluoroethyl or 1,1-difluoroethyl;

a group $ER^5$ in which E is O or S and $R^5$ is $C_1$- or $C_2$-alkyl which may carry from one to three fluorine atoms when $R^5$ is methoxy and from one to five fluorine atoms when $R^5$ is ethoxy, with the exception of difluoromethoxy;

nitro or hydroxyl; and $R^4$ is hydrogen, methyl, ethyl, methoxy, ethoxy, methylthio, ethylthio or $C_1$- or $C_2$-haloalkoxy, such as $C_1$ or $C_2$-fluoro- or chloroalkoxy, for example trifluoromethoxy, fluorine or chlorine, with the exception of 6-chloro and 6-fluoro when $R^3$ is alkyl or $C_1$- or $C_2$-alkoxy;

halogen is in general fluorine, chlorine, bromine or iodine.

Particular preference is given to compounds I where $R^1$ is methyl, $R^2$ and $R^4$ are each hydrogen and $R^3$ is trifluoromethoxy, to compounds I where $R^1$ is methyl, $R^2$ is hydrogen, $R^3$ is thiomethyl and $R^4$ is thiomethyl, in particular 6-thiomethyl, and to compounds I where $R^1$ is methyl, $R^2$ and $R^4$ are each hydrogen and $R^3$ is nitro or methoxy.

The novel sulfonylureas of the formula I are obtainable by various methods which are described in the literature. Particularly advantageous methods (A–D) are illustrated below by way of example.

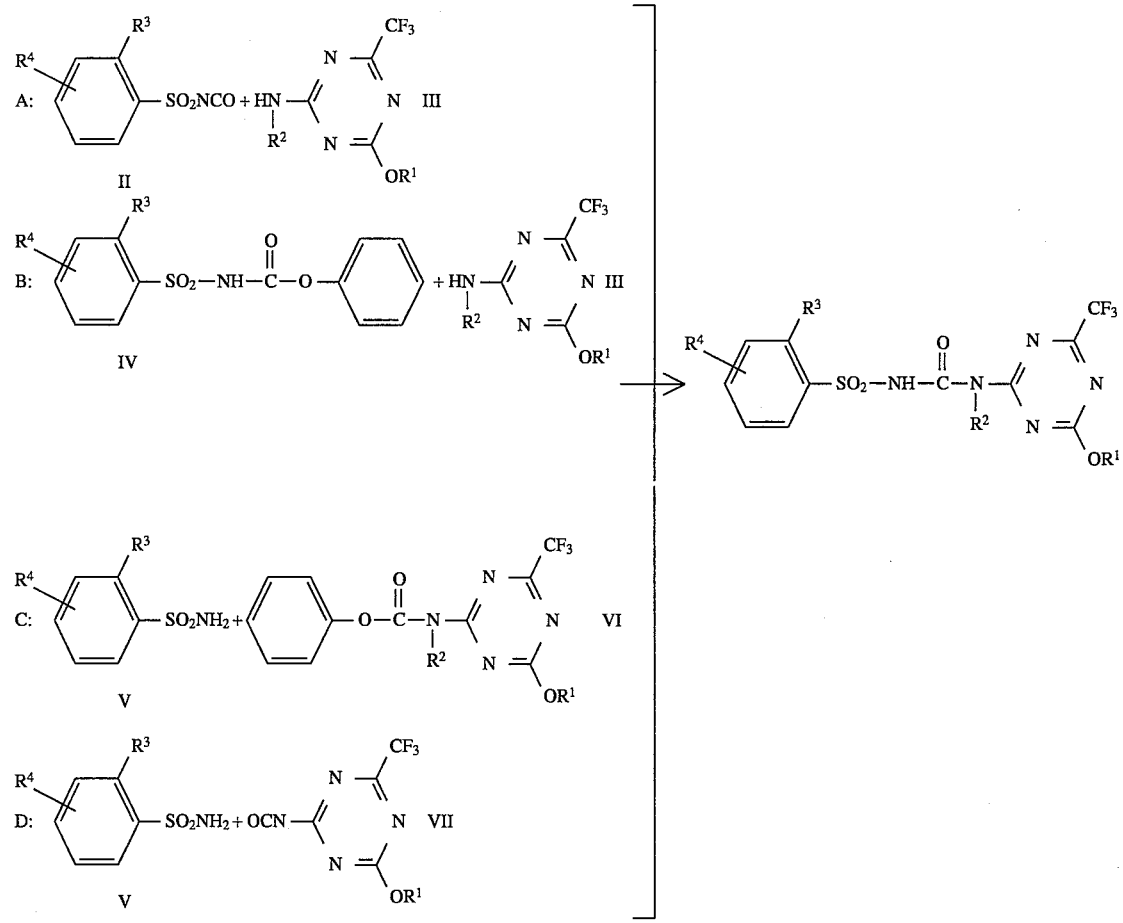

A: A sulfonylisocyanate II is reacted in a conventional manner (EP-A-162 723) with about the stoichiometric amount of a 2-amino-1,3,5-triazine derivative III at from 0° to 120° C., preferably from 10° to 100° C. The reaction can be carried out under atmospheric or superatmospheric pressure (up to 50 bar), preferably at from 1 to 5 bar, continuously or batchwise.

Solvents and diluents which are inert under the particular reaction conditions are advantageously used for the reactions. Examples of suitable solvents are halohydrocarbons, in particular chlorohydrocarbons, eg. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,2- or 1,1,2-trichloroethane, trichloroethyloene or pentachloroethane, o-, m- or p-difluorobenzene, 1,2-dichloroethane, 1,2-dichloroethane, 1,2-cis-dichloroethylene, chlorobenzene, fluorobenzene, bromobenzene, iodobenzene, o-, m- or p-dichlorobenzene, o-, p- or m-dibromobenzene, o-, m- or p-chlorotoluene or 1,2,4-trichlorobenzene; ethers, eg. ethyl propyl ether, methyl tert-butyl ether, n-butyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole or β,β'-dichlorodiethyl ether; nitrohydrocarbons, such as nitromethane, nitroethane, nitrobenzene, o-, m- or p-chloronitrobenzene or o-nitrotoluene; nitriles, such as acetonitrile, butyronitrile, isobutyronitrile, benzonitrile or m-chlorobenzonitrile; aliphatic or cycloaliphatic hydrocarbons, eg. heptane, pinane, nonane, o-, m- or p-cymene, gasoline fractions boiling within a range from 70° to 190° C., cyclohexane, methylcyclohexane, decaline, petroleum ether, hexane, naphtha, 2,2,4-trimethylpentane, 2,2,3-trimethylpentane, 2,3,3-trimethylpentane or octane; esters, eg. ethyl acetate, ethyl acetoacetate or isobutyl acetate; amides, eg. formamide, methylformamide or dimethylformamide; ketones, eg. acetone or methyl ethyl ketone, and corresponding mixtures. The solvent is advantageously used in an amount of from 100 to 2,000, preferably from 200 to 700, % by weight, based on the starting material II.

The compound II required for the reaction is generally used in about equimolar amounts (for example from 80 to 120%, based on the particular starting material III). The starting material III in one of the abovementioned diluents can be initially taken and the starting material II then added.

However, the process for the preparation of the novel compounds is advantageously carried out by initially taking the starting material II, if necessary in one of the abovementioned diluents, and then adding the starting material III.

To terminate the reaction, stirring is carried out for a further 20 minutes to 24 hours at from 0° to 120° C., preferably from 10° to 100° C., after the addition of the components.

A tertiary amine, for example pyridine, α,β-γ-picoline, 2,4- or 2,6-lutidine, 2,4,6-collidine, p-dimethylaminopyridine, trimethylamine, triethylamine, tri-n-propylamine, 1,4-diaza[2.2.2]bicyclooctane [DABCO] or 1,8-diazabicyclo[2.4.0]undec-7-ene, may advantageously be used as a reaction accelerator, in an amount of from 0.01 to 1 mol per mol of starting material II.

The end product I is isolated from the reaction mixture in a conventional manner, for example after distilling off solvents or directly by filtration under suction. The remaining residue may furthermore be washed with water or dilute acid to remove basic impurities. However, the residue can also be dissolved in a water-immiscible solvent and washed in the manner described. The desired end products are obtained in pure form; if necessary, they can be purified by recrystallization, stirring in an organic solvent which takes up impurities or chromatography.

This reaction is preferably carried out in acetonitrile, methyl tert-butyl ether, toluent or methylene chloride in the presence of from 0 to 100, preferably from 0 to 50, molar equivalents of a tertiary amine, such as 1,4-diazabicyclo [2.2.2.]octane or triethylamine.

B: A corresponding sulfonyl carbamate of the formula IV is reacted in a conventional manner (EP-A-120 814, EP-A-101 407), in an inert organic solvent at from 0° to 120° C., preferably from 10° to 100° C., with a 2-amino-1,3,5-triazine derivative III. Bases, such as tertiary amines, may be added here, with the result that the reaction is accelerated and the product quality improved.

Suitable bases for this purpose are, for example, tertiary amines as stated under A, in particular triethylamine or 1,4-diazabicyclo[2.2.2]octane, in an amount of from 0.01 to 1 mol per mol of starting material IV.

Advantageously used solvents are those stated under A.

The solvent is used in an amount of from 100 to 2,000, preferably from 200 to 700, % by weight, based on the starting material IV.

The compound IV required for the reaction is generally used in about equimolar amounts (for example from 80 to 120%, based on the particular starting material III). The starting material IV in one of the abovementioned diluents may be initially taken and the starting material III then added.

However, the starting material III in one of the stated solvents or diluents may furthermore be initially taken and the sulfonyl carbamate IV added.

In both cases, a base is added as a catalyst before or during the reaction.

The end product I can be obtained from the reaction mixture in a conventional manner, as stated under A.

C: A sulfonamide of the formula V is reacted in a conventional manner (EP-A-141 777 and EP-A-101 670), in an inert organic solvent, with about the stoichiometric amount of a phenyl carbamate VI at from 0° to 120° C., preferably from 20° to 100° C. The reaction can be carried out at atmospheric or superatmospheric pressure (up to 50 bar), preferably at from 1 to 5 bar, continuously or batchwise.

Bases such as tertiary amines, which accelerate the reaction and improve the product quality, may be added here. Suitable bases for this purpose are those stated under A, in particular triethylamine, 2,4,6-collidine, 1,4-diazabicyclo [2.2.2]octane [DABCO] or 1,8-diazabicyclo[ 5.4.0]undec-7-ene (DBU), in an amount of from 0.01 to 1 mol per mol of starting material V.

Advantageously used solvents or diluents are those stated under A.

The solvent is used in an amount of from 100 to 2,000, preferably from 200 to 700, % by weight, based on the starting material V.

The compound V required for the reaction is generally used in about equimolar amounts (for example from 80 to 120%, based on the particular starting materials VI). The starting material VI in one of the abovementioned diluents may be initially taken and the starting material V then added.

However, the starting material V in one of the stated solvents may also be initially taken and the carbamate VI then added. In both cases, one of the stated bases may be added as a catalyst before or during the reaction.

To terminate the reaction, stirring is carried out for a further 20 minutes to 24 hours at from 0° to 120° C., preferably from 10° to 100° C., in particular from 20° to 80° C., after the addition of the components.

The sulfonylureas of the formula I are isolated from the reaction mixture by conventional methods as described under A.

D: A sulfonamide of the formula V is reacted in a conventional manner (EP-A-234 352), in an inert organic solvent, with about the stoichiometric amount of isocyanate VII at from 0° to 150° C., preferably from 10° to 100° C. The reaction can be carried out under atmospheric or superatmosperic pressure (up to 50 bar), preferably at from 1 to 5 bar, continuously or batchwise.

Bases such as tertiary amines, which accelerate the reaction and improve the product quality, may be added before or during the reaction. Suitable bases for this purpose are those stated under A, in particular triethylamine or 2,4,6-collidine, in an amount of from 0.01 to 1 mol per mol of starting material V.

Advantageously used solvents are those stated under A. The solvent is used in an amount of from 100 to 2,000, preferably from 200 to 700, % weight, based on the starting material V.

The compound V required for the reaction is generally used in about equimolar amounts (for example from 80 to 120%, based on the particular starting materials VII). The starting material VII in one of the stated diluents may be initially taken and the starting material V then added. However, the sulfonamide may also be initially taken and the isocyanate VII then added.

To terminate the reaction, stirring is carried out for a further 20 minutes to 24 hours at from 0° to 120° C., preferably from 10° to 100° C., in particular from 20° to 80° C., after the addition of the components. The end product I can be obtained from the reaction mixture in the conventional manner, as described under A.

The sulfonylisocyanates of the formula II which are required for the starting materials can be obtained in a conventional manner from the corresponding sulfonamides by phosgenation (Houben-Weyl 11/2 (1985) 1106, U.S. Pat. No. 4,379,769) or by reacting the sulfonamide with chlorosulfonyl isocyanate (German Laid-Open Application DOS 3,132,944).

The sulfonamides of the formula V can be obtained by reacting the corresponding sulfonyl chlorides with ammonia (M. Quaedvlieg in Houben-Weyl, Methoden der Organiachen Chemie, Georg Thieme Verlag, Stuttgart, 9 (1955), 398–400, F. Muth, ibid., 605 et seq.). However, it is also possible for an o-halobenzenesulfonamide to be subjected to a nucleophilic substitution, for example with an alcohol or thiol, and, for example, for the resulting thioether to be oxidized to the sulfoxide or sulfone (cf. process examples).

The corresponding sulfonyl chlorides for the preparation of the sulfonamides of the formula V are obtained in general by a Meerwein reaction (diazotization of suitable amides and sulfochlorination with sulfur dioxide and a catalysis by a copper salt: F. Muth in Houben-Weyl, Methoden der organischen Chemie, Georg Thieme Verlag, Stuttgart, 9 (1955), 579, S. Pawlenko in Houben-Weyl, Methoden der organischen Chemie, Georg Thieme Verlag, E 11/2 (1985), 1069), from the corresponding sulfonic acids (F. Muth in Houben-Weyl, Methoden der organischen Chemie, Georg Thieme Verlag, Stuttgart, 9 (1955), 564, by chlorosulfonation of suitable aromatic intermediate (F. Muth, ibid., page 572) or by oxidative chlorination at low-valence sulfur states (mercaptans, diaryl disulfides or S-benzylmercaptans) (F. Muth, ibid., page 580, S. Pawlenko, loc, cit., page 1073).

The sulfonyl carbamates of the formula IV were prepared by conventional reactions or reactions similar to these (for example EP-A 120 814). However, the sulfonylisocyanates of the formula II, in an inert solvent, such as ether or dichloromethane, can also be converted with phenol into the carbamates of the formula IV.

Carbamates of the formula VI are obtainable by known reactions or by reactions similar to these (for example EP-A 101 670), but can also be prepared from the corresponding isocyanates VII by reaction with phenol.

The isocyanates of the formula VII are obtained from the amines of the formula III by treatment with oxalyl chloride or phosgene (similarly to Angew. Chem. 83 (1971), 407 or EP-A 388 873).

2-Amino-4-methoxy-6-trifluoromethyl-1,3,5-triazine and 2-amino-4-ethoxy-6-trifluoromethyl-1,3,5-triazine are known from the literature (Yakugaku Zasshi 95 (1975), 499).

The salts of the compounds I are obtainable in a conventional manner (EP-A-304 282 or U.S. Pat. No. 4,599,412). They are obtained by deprotonation of the corresponding sulfonylureas I in water or in an inert organic solvent at from –80° to 120° C., preferably from 0° to 60° C., in the presence of a base.

Examples of suitable bases are alkali metal or alkaline earth method hydroxides, hydrides, oxides or alcholates, such as sodium hydroxide, potassium hydroxide, lithium hydroxide, sodium methylate, sodium ethylate, sodium tertbutylate, sodium hydride, calcium hydride and calcium oxide.

Examples of suitable solvents in addition to water are alcohols, such as methanol, ethanol or tertbutanol, ethers, such as tetrahydrofuran and dioxane, acetonitrile, dimethylformamide, ketones, such as acetone or methyl ethyl ketone, and also halohydrocarbons.

The deprotonation can be carried out at atmospheric pressure or at up to 50 bar, preferably from atmospheric pressure to superatmospheric pressure of 5 bar.

The compounds I or herbicidal agents containing them, and their environmentally compatible alkali metal or alkaline earth metal salts, combat injurious plants very well in crops such as wheat, rice and Indian corn without damaging the crop plants—an effect which occurs particularly at low application rates. The compounds may be applied by instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purposes for which the agents are being used, but they must ensure as fine a distribution of the active ingredients according to the invention as possible.

The compounds I are generally suitable for the preparation of solutions, emulsions, pastes and oil dispersions to be sprayed direct. Examples of inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc.

Aqueous formulations may be prepared from emulsion concentrates, pastes, oil dispersions, wettable powders or water-dispersible granules by adding water. To prepare emulsions, pastes and oil dispersions and the ingredient as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methyl cellulose.

Powders, dusts and broadcasting agents may be prepared by mixing or grinding the active ingredients with a solid carrier.

Granules, e.g., coated, impregnated or homogenous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nut shell meal, cellulosic powders, etc.

The formulations contain from 0.01 to 95, and preferably 0.5 to 90, % by weight of active ingredient.

Example of formulations are as follows:

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 moles of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 26 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 8 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 10 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 5 is intimately mixed with 97 parts by weight of particulate kaolin. A dust is obtained containing 3% by weight of the active ingredient.

VII. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1 is intimately mixed with 2 parts of the calcium salt of dodecybenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

Application may be effected pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stage, and are from 0.001 to 3, preferably 0.01 to 1, kg of active ingredient per hectare.

In view of the numerous application methods possible, the compounds according to the invention, or agents containing them, may be used in a large number of crops. Those which follow are given by way of example:

| | |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Brassica napus* var. *napus* | rapeseed |
| *Brassica napus* var. *napobrassica* | swedes |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus sinensis* | orange trees |
| *Coffea arabica* (*Coffea canephora, Coffea liberica*) | coffee plants |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum, Gossypium herbaceum, Gossypium vitifolium*) | cotton |
| *Helianthus annuus* | sunflowers |
| *Hevea brasiliensis* | rubber plants |

| | |
|---|---|
| Hordeum vulgare | barley |
| Humulus lupulus | hops |
| Ipomoea batatas | sweet potatoes |
| Juglans regia | walnut trees |
| Lens culinaris | lentils |
| Linum usitatissium | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea europaea | olive trees |
| Oryza sativa | rice |
| Phaseolus lunatus | limabeans |
| Picea abies | Norway spruce |
| Pinus spp. | pine trees |
| Pisum sativum | English peas |
| Prunus avium | cherry trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cacao plants |
| Trifolium pratense | red clover |
| Triticum aestivum | wheat |
| Triticum durum | wheat |
| Vicia faba | tick beans |
| Vitis vinifera | grapes |
| Zea mays | Indian corn, sweet corn, maize |

To increase the spectrum of action and to achieve synergistic effects, the triazinyl-substituted sulfonylureas of the formula I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)-aryloxyphenoxypropionic acids and salts, esters, amides thereof, etc.

It may also be useful to apply the compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

Examples illustrating the synthesis of compounds I are given below.

A. Preparation of the intermediates 2-(2-Chloro-1,1,2-trifluoroethoxy)-benzenesulfonamide At 25 bis 30° C. and while stirring, 5.9 g (0.093 mol) of 88% strength potassium hydroxide powder was added over a period of 5 minutes to a solution of 28.4 g (0.164 Mol) of 2-hydroxybenzenesulfonamide in 200 ml of acetone. At 40° to 50° C. and while stirring, 29.6 g (0.254 mol) of chlorotrifluoroethylene was gassed in over a period of 12 hours. The precipitate was filtered off under such and washed with acetone. The filtrate was evaporated down under reduced pressure, stirred into 700 ml of water, suction filtered, washed and dried. There was obtained 28.8 g (60.7%) of the title compound of m.p. 113° to 116° C.

B. Preparation of active ingredients I 1.
2-Nitro-1-N[(4-methoxy-6-trifluoromethyl-1,3,5-triazin-2-yl)aminocarbonyl]benzenesulfonamide At 25° C., 3.5 g (15.5 mmol) of 2-nitrobenzenesulfonyl isocyanate in 10 ml of 1,2-dichlorethane was added to a mixture of 3.0 g (15.5 mmol) of 2-amino-4-methoxy-6-trifluoromethyltriazine in 150 ml of 1,2-dichloroethane. After this mixture had been stirred for 14 hours at 25° C. the solvent was removed under reduced pressure at 40° C. and the solid residue was stirred with methyl tert-butyl ether. The product was suction filtered and dried under reduced pressure at 50° C. There was obtained 4.6 g (70.3% of theory) of the title compound, decomposing at 159° C.

2. Sodium (2-nitro-1-N-[(4-methoxy-6-trifluoromethyl-1,3,5-triazin-2-yl)aminocarbonyl]benzenesulfonamide At 25° C. 0.65 g (3.6 mmol) of a solution of sodium methanolate (30 wt % strength) in methanol was added to a suspension of 1.5 g (2.6 mmol) of 2-nitro-1-N-[(4-methoxy-6-trifluoromethyl- 1,3,5-triazin-2-yl)aminocarbonyl]benzenesulfonamide in 30 ml of methanol. After stirring for one hour at 25° C. the homogeneous solution was evaporated down under a water-jet vacuum at 50° C., the title compound (decomposition point: 161° C.) being obtained in quantitative yield.

The active ingredients listed in Table 1 below were obtained analogously.

TABLE 1

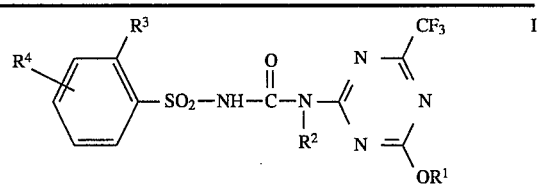

| Active ingredient no. | $R^1$ | $R^2$ | $R^3$ | $R^4$ | m.p. [°C.] |
|---|---|---|---|---|---|
| 1 | $CH_3$ | H | $NO_2$ | H | 159 decomp. |
| 2 | $CH_3$ | H | $NO_2$ | H | 161 decomp. Na salt |
| 3 | $CH_3$ | H | $OCH_3$ | H | |
| 4 | $CH_3$ | H | $OC_2H_5$ | H | |
| 5 | $CH_3$ | H | $OCF_3$ | H | 153–156 |
| 6 | $CH_3$ | H | $OCF_3$ | H | 143–145 decomp. Na salt |
| 7 | $CH_3$ | H | $OCF_2CH_3$ | H | |
| 8 | $CH_3$ | H | $OCF_2CF_2H$ | H | 150–152 |
| 9 | $CH_3$ | H | $OCF_2CF_3$ | H | |
| 10 | $CH_3$ | H | $CH_3$ | H | 173–175 |
| 11 | $CH_3$ | H | $C_2H_5$ | H | |
| 12 | $CH_3$ | H | $CH_2Cl$ | H | |
| 13 | $CH_3$ | H | $CH_2CH_2Cl$ | H | |
| 14 | $CH_3$ | H | $CH_2OCH_3$ | H | |
| 15 | $CH_3$ | H | $CH_2CH_2OCH_3$ | H | |
| 16 | $CH_3$ | H | $CF_2CH_3$ | H | |
| 17 | $CH_3$ | H | $CF_2CF_3$ | H | |

TABLE 1-continued

[Structure I: R⁴-phenyl with R³ ortho, SO₂—NH—C(=O)—N(R²)—[triazine with CF₃ and OR¹]]

| Active ingredient no. | R¹ | R² | R³ | R⁴ | m.p. [°C.] |
|---|---|---|---|---|---|
| 18 | CH₃ | H | SCHF₂ | H | |
| 19 | CH₃ | H | SCF₃ | H | |
| 20 | CH₃ | H | OCF₂CF₂H | H | 179 decomp. Na salt |
| 21 | CH₃ | H | CCl₃ | H | 176 |
| 22 | CH₃ | H | CCl₃ | H | 131 decomp. Na salt |
| 23 | CH₃ | H | OH | H | 186 |
| 24 | CH₃ | H | SCH₃ | H | 160–161 |
| 25 | CH₃ | H | SCH₃ | H | 130–140 decomp. Na salt |
| 26 | CH₃ | H | SCH₃ | 6-SCH₃ | |
| 27 | CH₃ | H | SCH₃ | 6-SCH₃ | Na salt |
| 28 | CH₃ | H | OCH₂CF₃ | 5-OCH₂CF₃ | 157–161 |
| 29 | CH₃ | H | OCH₂CF₃ | 5-OCH₂CF₃ | 151 decomp. Na salt |
| 30 | CH₃ | H | OCH₃ | 5-OCH₃ | 172–175 |

The compounds listed below may be obtained analogously:

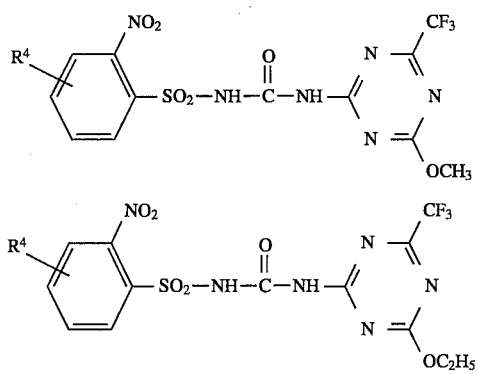

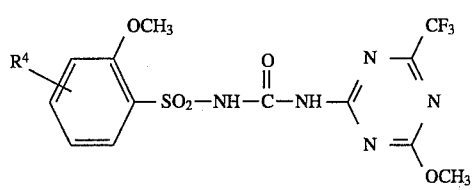

or their Na salts, R⁴ having the following meanings:
hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 3-chloro, 4-chloro, 5-chloro, 3-methoxy, 4-methoxy, 5-methoxy, 6-methoxy, 3-ethoxy, 4-ethoxy, 5-ethoxy, 6-ethoxy, 6-methylthio;

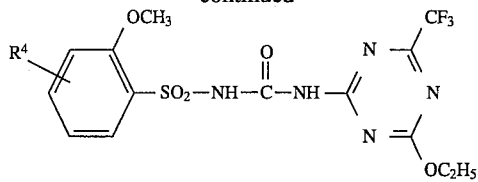

or their Na salts, R⁴ having the following meanings:
hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy, 6-methylthio;

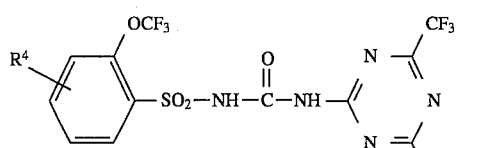

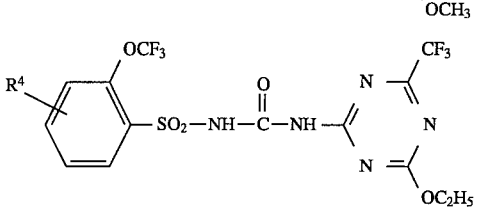

or their Na salts, R⁴ having the following meanings:
hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy, 6-methylthio;

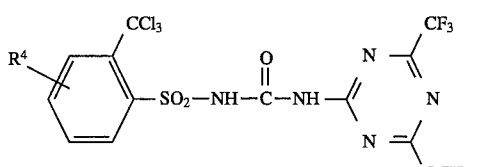

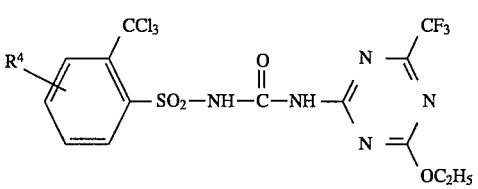

or their Na salts, R⁴ having the following meanings: hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy, 6-methylthio;

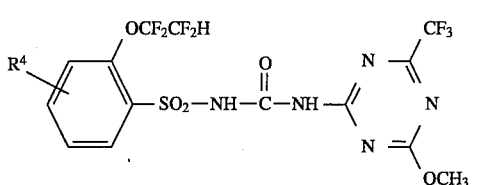

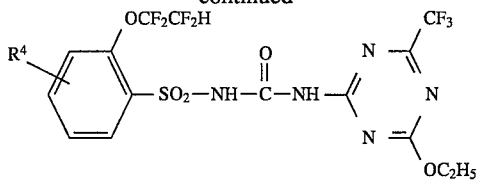

or their Na salts, $R^4$ having the following meanings:

hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy, 6-methylthio;

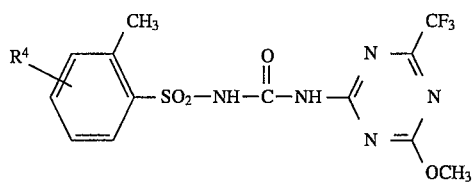

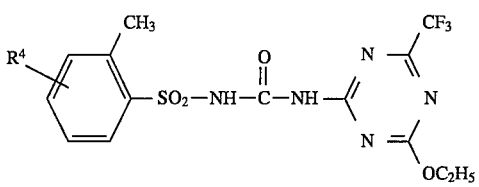

or their Na salts, $R^4$ having the following meanings:

hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 3-chloro, 4-chloro, 5-chloro, 3-methoxy, 4-methoxy, 5-methoxy, 6-methoxy, 3-ethoxy, 4-ethoxy, 5-ethoxy, 6-ethoxy, 6-methylthio;

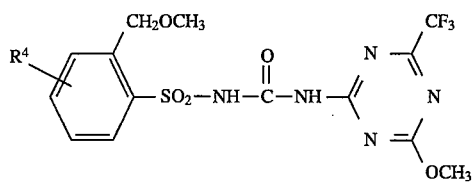

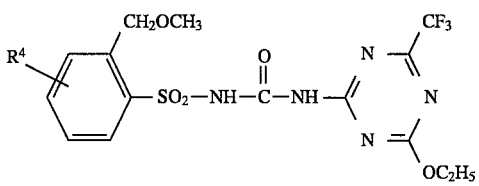

or their Na salts, $R^4$ having the following meanings:

hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy, 6-methylthio;

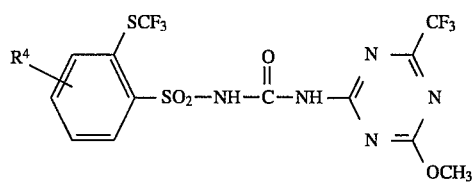

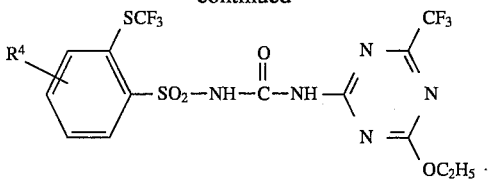

or their Na salts, $R^4$ having the following meanings:

hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy, 6-methylthio;

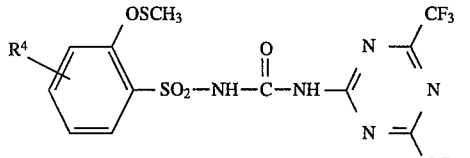

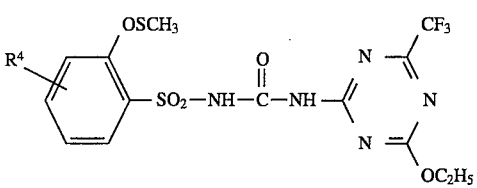

or their Na salts, $R^4$ having the following meanings:

hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy, 6-methylthio.

Use examples:

The herbicidal action of N-[(1,3,5-triazin-2-yl)aminocarbonyl]-benzenesulfonamides of the formula I on the growth of test plants is demonstrated in the following greenhouse experiments.

The vessels employed were plastic flowerpots having a volume of 300 cm$^3$ and filled with a sandy loam containing about 3.0% humus. The seeds of the test plants were sown shallow, and separately, according to species.

For the postemergence treatment, plants were used which had been sown in the pots and grown there, or they were grown separately as seedlings and transplanted to the pots a few days before treatment.

The plants were grown, depending on growth form, to a height of 3 to 15 cm before being treated with the active ingredients, which were suspended or emulsified in water and sprayed through finely distributing nozzles. The application rates of postemergence treatment were 250, 125, 60, and 30 g/ha.

The pots were set up in the greenhouse, heat-loving species at from 20° to 35° C., and species from moderate climates at from 10° to 20° C. The experiments were run for from 2 to 4 weeks. During this period the plants were tended and their reactions to the various treatments assessed.

The assessment scale was 0 to 100, 100 denoting non-emergence or complete destruction of at least the visible plant parts, and 0 denoting no damage or normal growth.

The plants used in the greenhouse experiments were Amaranthus retroflexus, Chenopodium album, Solanum nigrum and Triticum aestivum.

Example No. 1, employed postemergence at a rate of 0.06 kg/ha, provides very good control of unwanted broadleaved plants and is excellently tolerated by wheat.

The comparative experiments described below demonstrate the advantageous herbicidal properties of the compounds according to the invention in comparison to the art compounds D₂ (EP-A 44 808) and A (U.S. Pat. No. 4,120, 691 or DE-A 27 15 786)

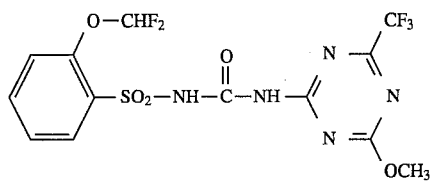

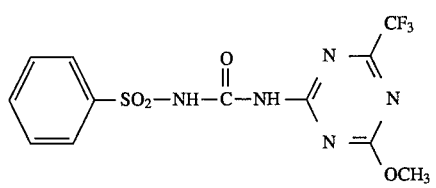

Comparative Experiment I

Comparison of the results of greenhouse experiments carried out postemergence at application rates of 0.06 and 0.03 kg/ha of active ingredient

|  | Damage in % | | | |
| --- | --- | --- | --- | --- |
|  | Example 5 | | D₂ | |
|  | 0.06 kg/ha | 0.03 kg/ha | 0.06 kg/ha | 0.03 kg/ha |
| Test plants | | | | |
| ZEAMX | 10 | 0 | 55 | 15 |
| ABUTH | 100 | 100 | 65 | 25 |
| AMARE | 100 | 100 | 85 | 80 |
| POLPE | 98 | 80 | 60 | 50 |
| SOLNI | 100 | 100 | 15 | 15 |

Comparative Experiment II

Comparison of the results of greenhouse experiments carried out postemergence at application rates of 0.06 and 0.03 kg/ha of active ingredient

|  | Damage in % | | | |
| --- | --- | --- | --- | --- |
|  | Example 1 | | A | |
|  | 0.06 kg/ha | 0.03 kg/ha | 0.06 kg/ha | 0.03 kg/ha |
| Test plants | | | | |
| TRZAS | 0 | 0 | 0 | 0 |
| AMARE | 100 | 70 | 80 | 70 |
| GALAP | 85 | 85 | 60 | 50 |
| SOLNI | 70 | 70 | 15 | 15 |

The abbreviations used for the test plants denote the following species:

| Abbreviation | Botanical name | Common name |
| --- | --- | --- |
| ABUTH | *Abutilon theophrasti* | velvetleaf |
| AMARE | *Amaranthus retroflexus* | redroot pigweed |
| GALAP | *Galium aparine* | catchweed bedstraw |
| POLPE | *Polygonum persicaria* | ladysthumb |
| SOLNI | *Solanum nigrum* | black nightshade |
| TRZAS | *Triticum aestivum* | spring wheat |
| ZEAMX | *Zea mays* | Indian corn |

We claim:

1. An N-((1,3,5-triazin-2-yl)-aminocarbonyl)-benzenesulfonamide of the formula I

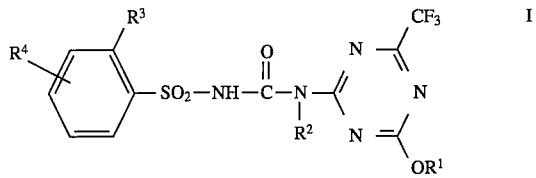

where $R^1$ is methyl or ethyl;

$R^2$ is hydrogen or methyl;

$R^3$ is $C_2$–$C_4$-haloalkyl; or $R^3$ is a group $ER^5$ in which E is O or S and $R^5$ is $C_1$-alkyl which carries from 1 to 3 fluorine atoms or $C_2$-alkyl which carries form 1 to 5 fluorine atoms, with the exception of difluoromethoxy; and $R^4$ is hydrogen, methyl, ethyl, methoxy, ethoxy, methylthio, ethylthio, $C_1$- or $C_2$-haloalkoxy, fluorine or chlorine;

and agriculturally useful salts thereof.

2. An N-[(1,3,5-triazin-2-yl)-aminocarbonyl]-benzenesulfonamide of the formula I as defined in claim 1, wherein $R^1$ is methyl, $R^2$ and $R^4$ are each hydrogen and $R^3$ is trifluoromethoxy.

3. A herbicidal composition containing an N-[(1,3,5-triazin-2-yl)-aminocarbonyl]-benzenesulfonamide of the formula I as defined in claim 1 or its salt and conventional carriers.

4. A method for controlling undesirable plant growth, wherein a herbicidal amount of an N-[(1,3,5-triazin- 2-yl)-aminocarbonyl]-benzenesulfonamide of the formula I as defined in claim 1 or of one of its salts is allowed to act on the plants or their habitat.

* * * * *